United States Patent
Sorenson et al.

(10) Patent No.: US 11,826,577 B2
(45) Date of Patent: Nov. 28, 2023

(54) IMPEDANCE MEASUREMENT CIRCUIT ARCHITECTURE

(71) Applicant: Medtronic, Inc., Minneapolis, MN (US)

(72) Inventors: Scott G. Sorenson, Lakeville, MN (US); Michael Kemmerer, Victoria, MN (US)

(73) Assignee: Medtronic, Inc., Minneapolis, MN (US)

( * ) Notice: Subject to any disclaimer, the term of this patent is extended or adjusted under 35 U.S.C. 154(b) by 239 days.

(21) Appl. No.: 17/185,178

(22) Filed: Feb. 25, 2021

(65) Prior Publication Data

US 2022/0266044 A1    Aug. 25, 2022

(51) Int. Cl.
*A61N 1/37*     (2006.01)
*A61N 1/39*     (2006.01)

(52) U.S. Cl.
CPC .............. *A61N 1/3937* (2013.01); *A61N 1/37* (2013.01); *A61N 1/3962* (2013.01); *A61N 1/3968* (2013.01)

(58) Field of Classification Search
CPC ................................. A61N 1/3937; A61N 1/37
See application file for complete search history.

(56) References Cited

U.S. PATENT DOCUMENTS

| | | | |
|---|---|---|---|
| 5,910,156 A | 6/1999 | Cinbis et al. | |
| 6,181,969 B1 * | 1/2001 | Gord | A61N 1/32 607/57 |
| 6,317,633 B1 | 11/2001 | Jorgenson et al. | |
| 6,445,951 B1 | 9/2002 | Mouchawar | |
| 6,597,950 B2 | 7/2003 | Inder et al. | |
| 6,895,280 B2 | 5/2005 | Meadows et al. | |

(Continued)

FOREIGN PATENT DOCUMENTS

WO    2000043065 A1    7/2000

OTHER PUBLICATIONS

Rout et al., "A Subthreshold Source-Coupled Logic based Time-Domain Comparator for SAR ADC based Cardiac Front-Ends," 2019 IEEE Asia Pacific Conference on Circuits and Systems (APCCAS), Nov. 2019, 4 pp.

(Continued)

*Primary Examiner* — Eric D. Bertram
(74) *Attorney, Agent, or Firm* — Shumaker & Sieffert, P.A.

(57) ABSTRACT

A lead impedance stimulation architecture and a dual current source and sink methodology to output a biphasic current pulse and measure a resulting induced voltage across the stimulation electrodes to determine lead impedance. A common mode capacitance on the electrode interface may have little impact on the stimulation architecture of this disclosure allowing for fast voltage rise time and consistent and accurate impedance measurement. In addition, the dual source and sink includes a monitor circuit on each of the source and the sink circuitry. In the event of an open circuit indicating a lead breakage, loose connection, lead migration, insulation leak, and so on, the monitor circuit may provide an output to indicate specifically which electrode is unable to reach the correct current stimulation amplitude. In this manner the techniques of this disclosure, may also detect a lead break in a single lead impedance measurement.

25 Claims, 9 Drawing Sheets

(56) References Cited

U.S. PATENT DOCUMENTS

| | | | |
|---|---|---|---|
| 7,593,766 B2 | 9/2009 | Faber et al. | |
| 7,877,139 B2 | 1/2011 | Ostroff | |
| 7,890,163 B2 | 2/2011 | Belalcazar | |
| 8,170,682 B2 | 5/2012 | Greenberg et al. | |
| 8,209,005 B1 | 6/2012 | Moulder et al. | |
| 8,311,639 B2 | 11/2012 | Parker et al. | |
| 8,417,333 B2 | 4/2013 | Linder et al. | |
| 8,452,394 B2 | 5/2013 | Burnes et al. | |
| 8,473,069 B2 | 6/2013 | Bi et al. | |
| 8,606,362 B2* | 12/2013 | He | A61N 1/0551 607/46 |
| 8,738,135 B1* | 5/2014 | Lee | A61B 5/24 607/122 |
| 8,886,337 B2 | 11/2014 | Bennett et al. | |
| 9,014,807 B2 | 4/2015 | Bocek et al. | |
| 9,056,206 B2* | 6/2015 | Torgerson | A61N 1/36125 |
| 9,295,404 B2 | 3/2016 | Valvano et al. | |
| 9,616,233 B2 | 4/2017 | Shi et al. | |
| 10,022,540 B2 | 7/2018 | Bradley et al. | |
| 10,668,277 B2 | 6/2020 | Gunderson et al. | |
| 10,912,942 B2* | 2/2021 | Weerakoon | A61N 1/025 |
| 11,071,864 B2* | 7/2021 | Boor | A61N 1/36062 |
| 11,173,308 B2* | 11/2021 | Brill | A61B 5/24 |
| 11,179,566 B2* | 11/2021 | Smith | A61N 1/36146 |
| 11,195,609 B2* | 12/2021 | Mustakos | G16H 40/60 |
| 2001/0007056 A1* | 7/2001 | Linder | A61N 1/3925 600/547 |
| 2005/0267546 A1* | 12/2005 | Parramon | A61N 1/36071 607/48 |
| 2007/0038250 A1* | 2/2007 | He | A61N 1/0551 607/2 |
| 2007/0100399 A1* | 5/2007 | Parramon | A61N 1/0551 607/43 |
| 2007/0135868 A1* | 6/2007 | Shi | A61N 1/36071 607/62 |
| 2007/0244479 A1 | 10/2007 | Beatty et al. | |
| 2009/0156957 A1* | 6/2009 | Linder | A61N 1/3925 600/547 |
| 2009/0210020 A1 | 8/2009 | Feldman et al. | |
| 2010/0106219 A1* | 4/2010 | Torgerson | A61N 1/36185 607/59 |
| 2010/0106231 A1* | 4/2010 | Torgerson | A61N 1/36082 607/116 |
| 2010/0125315 A1* | 5/2010 | Parramon | A61N 1/36157 607/2 |
| 2011/0093041 A1* | 4/2011 | Straka | A61N 1/36125 607/59 |
| 2011/0276103 A1* | 11/2011 | Maile | A61N 1/362 607/9 |
| 2012/0071950 A1* | 3/2012 | Archer | A61N 1/36125 607/66 |
| 2018/0071516 A1* | 3/2018 | Weiss | A61N 1/36125 |
| 2018/0071520 A1* | 3/2018 | Weerakoon | A61N 1/37217 |
| 2019/0083796 A1* | 3/2019 | Weerakoon | H03K 5/26 |

OTHER PUBLICATIONS

"MOSFET Gate Drive Circuit—Application Note," from Toshiba Electronic Devices & Storage Corporation, Jul. 26, 2018, 22 pp.
International Search Report and Written Opinion of International Application No. PCT/US2022/015207, dated May 13, 2022, 10 pp.

* cited by examiner

IMPEDANCE MEASUREMENT CIRCUIT ARCHITECTURE

TECHNICAL FIELD

The disclosure relates to medical devices and specifically to measuring impedance by a medical device.

BACKGROUND

Medical devices that sense patient signals and/or deliver electrical therapy via one or more leads carried by one or more electrodes may also be configured to check for lead integrity, which is a check to ensure a good electrical connection between the sensing and/or therapy generation circuitry and the target tissue. One type of lead integrity test involves measurement of lead impedance.

To measure lead impedance, the medical device may output a current or a voltage through two or more electrodes on the lead, or leads, and measure the resulting voltage or current to calculate the impedance of the path including the electrodes using Ohm's Law. A relatively low value of impedance may indicate a good electrical connection. A lead impedance above a threshold impedance may indicate an issue, such as a lead breakage, loose connection, lead migration, insulation leak, and so on. A lead impedance that is too low, e.g., below a threshold, may indicate a short circuit.

A medical device may similarly measure impedance for other purposes. For example, a medical device may measure impedance to determine characteristics of the patient, e.g., of tissue proximate to the two or more electrodes. A medical device may measure impedance to determine a fluid status or monitor respiration of the patient, as examples.

SUMMARY

In general, the disclosure describes devices and techniques for measurement of impedance via electrodes of a medical device that, for example, enable consistent and accurate measurement of impedance. The techniques of this disclosure include an impedance measurement architecture and a dual current source and sink methodology to output a current signal, e.g., a current pulse and measure a resulting induced voltage across electrodes to determine the impedance. A common mode capacitance on the electrode interface may have little impact on the impedance measurement architecture of this disclosure, allowing for fast voltage rise time and consistent and accurate impedance measurement. In addition, the dual source and sink may include a monitor circuit on each of the source and the sink circuitry. In the event of an open circuit, e.g., indicating a lead breakage, loose connection, lead migration, insulation leak, and so on, the monitor circuit may provide an output to indicate specifically which electrode is unable to reach the correct current amplitude. In this manner, the techniques of this disclosure may also detect a lead fault in a single lead impedance measurement.

In one example, this disclosure describes an impedance measurement device includes a source stimulation circuit includes a first switch configured to control a source stimulation current; a first amplifier configured to drive a control terminal of the first switch; a sink stimulation circuit includes a second switch configured to control a sink stimulation current; a second amplifier configured to drive a control terminal of the second switch; a current source coupled to the source stimulation circuit and the sink stimulation circuit, such that a magnitude of the source stimulation current approximately equals a magnitude of the sink stimulation current.

In another example, this disclosure describes an implantable medical device comprising impedance measurement circuitry, wherein the impedance measurement circuitry comprises: a source stimulation circuit includes a first switch configured to control a source stimulation current; a first amplifier configured to drive a control terminal of the first switch; a sink stimulation circuit includes a second switch configured to control a sink stimulation current; a second amplifier configured to drive a control terminal of the second switch; a current source coupled to the source stimulation circuit and the sink stimulation circuit, such that a magnitude of the source stimulation current approximately equals a magnitude of the sink stimulation current.

In another example, this disclosure describes a method includes driving, by a first amplifier, a control terminal of a first switch, wherein an input terminal of the first amplifier is coupled to a current source; controlling, by the first switch and based on an output from the first amplifier, a source stimulation current, wherein the source stimulation current connects to a tissue of a patient; driving, by a second amplifier, a control terminal of a second switch, wherein an input terminal of the second amplifier is coupled to the current source; controlling, by the second switch and based on an output from the second amplifier, a sink stimulation current, wherein: the sink stimulation current connects to the tissue of the patient, a magnitude of the sink stimulation current is approximately equal to a magnitude of the source stimulation current, the source stimulation current and the sink stimulation current induce a voltage at the tissue of the patient.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
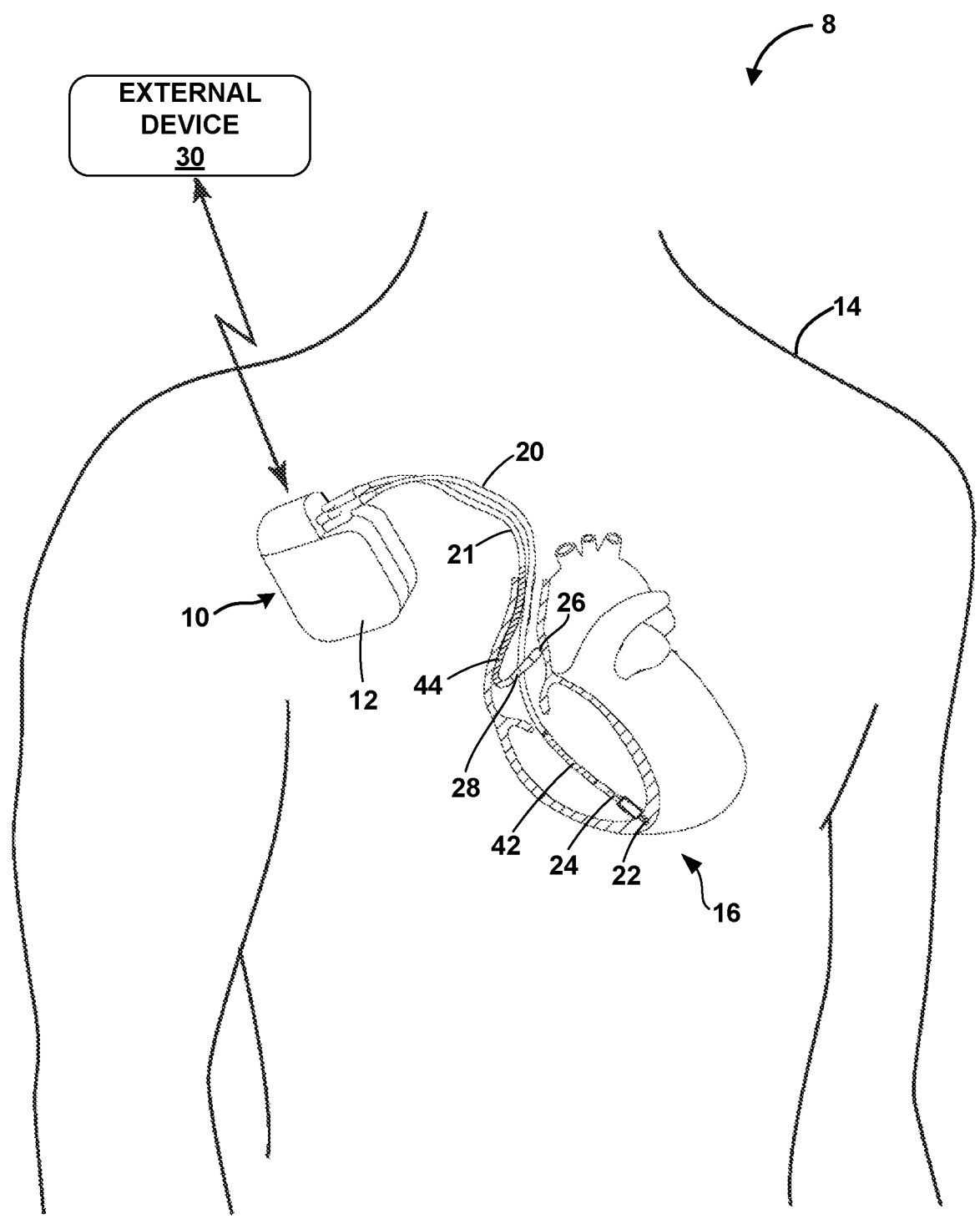
FIG. 1 is an example conceptual diagram of an implantable medical device system configured to measure impedance between two or more electrodes.

The disclosure describes techniques to measure lead impedance over a short period of time to obtain consistent and accurate measurement. A device that performs a lead impedance test, such as a medical device, may perform the lead impedance test between electrical stimulation therapy pulses and between time periods in which the medical device is taking other measurements. In the example of an implantable cardiac rhythm device, such as a pacemaker, cardioverter-defibrillator or cardiac resynchronization device, the device may measure cardiac tissue depolarization, and deliver pacing pulses or other electrical stimulation therapy throughout the cardiac cycle. Each cardiac cycle may be approximately one second or less, which leaves only a few fractions of a second to measure lead impedance and not interfere with other measurements or therapy delivery.

Medical device therapy and measurement circuitry may have a large amount of capacitance on the electrode interface because of circuitry used to improve bioelectrical measurement accuracy, patient safety, and therapy delivery. Some circuitry that may add to this capacitance may include channel capacitors, filter feed through capacitors, delivery circuit, blocking FETs, and so on. Some examples of existing lead impedance measurement circuit may perform a biphasic current stimulation and then measure the induced voltage across the stimulation electrodes to determine the lead impedance. Because of a short stimulation pulse width and a large amount of capacitance, the time constant to reach a DC steady state to take an impedance measurement may often be too long resulting in the final voltage measurement being inaccurate. The capacitance on the electrode interface may slow down the voltage rise so that the lead impedance measurement circuit may take a voltage sample while the voltage is changing, resulting in an inconsistent measurement.

In some examples, medical devices may use a stimulation difference measurement to avoid this inconsistent lead impedance result. For a stimulation difference measurement, the medical device may perform two or more current stimulations with different current amplitudes. The processor of the device may attempt to measure time constants and perform complex calculations to extract a lead impedance that would result in the measured time constant. The stimulation difference measurement may have a disadvantage because of the complicated procedure, intensive firmware, and processor operation. For a battery powered device, the extra processor operation awake time, and multiple stimulations may consume power and reduce battery life.

In contrast, the techniques of this disclosure include a lead impedance stimulation architecture and a dual current source and sink methodology. The techniques of this disclosure may no longer need to wait to slew and settle the common node capacitance on the electrode to tissue interface, which results in the voltage reaching a steady state value within a relatively short, e.g., less than 100 microsecond (µs), pulse width. In this manner the techniques of this disclosure enable a medical device to achieve a higher degree of measurement accuracy with reduced firmware burden and complexity, when compared to other techniques. In some examples, the techniques of this disclosure may also be used to measure a biological impedance, in addition to lead impedance.

In addition, the dual source and sink may include a monitor circuit on each of the source and the sink circuitry. In the event of an open circuit indicating a lead breakage, loose connection, lead migration, insulation leak, or similar connection issue, the monitor circuit may provide an output to indicate specifically which electrode is unable to reach the correct current stimulation amplitude. In this manner the techniques of this disclosure, may also detect a lead issue, e.g., a lead break or short, in a single lead impedance measurement. The monitor circuits of this disclosure may provide an advantage over other techniques that may performing a current stimulation on one electrode and ground a return electrode to complete the current path. In the event of an open circuit, such an existing circuit cannot differentiate which electrode is an open circuit without performing several other lead impedance measurements to determine the location of the open lead via a process of elimination.

FIG. 1 is an example conceptual diagram of an implantable medical device system configured to measure impedance between two or more electrodes. As illustrated in FIG. 1, a medical device system 8 for sensing cardiac events (e.g., P-waves and R-waves) and detecting and treating arrhythmia episodes, may include an implantable medical device (IMD) 10, a ventricular lead 20 and an atrial lead 21. In one example, IMD 10 may be an implantable cardioverter-defibrillator (ICD) capable of delivering pacing, cardioversion, and defibrillation therapy to the heart 16 of a patient 14. In other examples, IMD 10 may be a pacemaker capable of delivering pacing therapy, including anti-tachycardia pacing (ATP), bradycardia pacing and/or cardiac resynchronization therapy to the patient, but need not include the capability of delivering cardioversion or defibrillation therapies.

Ventricular lead 20 and atrial lead 21 are electrically coupled to IMD 10 and extend into the heart 16 of patient 14. Ventricular lead 20 includes electrodes 22 and 24 shown positioned on the lead in the patient's right ventricle (RV) for sensing ventricular EGM signals and pacing in the RV. Atrial lead 21 includes electrodes 26 and 28 positioned on the lead in the patient's right atrium (RA) for sensing atrial EGM signals and pacing in the RA.

In the example of FIG. 1, ventricular lead 20 additionally carries a high voltage coil electrode 42, and atrial lead 21 carries a high voltage coil electrode 44, used to deliver cardioversion and defibrillation shock pulses. In other examples, ventricular lead 20 may carry both of high voltage coil electrodes 42 and 44 or may carry a high voltage coil electrode in addition to those illustrated in the example of FIG. 1. Both ventricular lead 20 and atrial lead 21 may be used to acquire cardiac EGM signals and impedance signals from patient 14 and to deliver therapy in response to the acquired data. Medical device system 8 is shown as a dual chamber ICD including atrial lead 21 and ventricular lead 20, but in some embodiments, system 8 may be a dual or multi-chamber system including a coronary sinus lead extending into the right atrium, through the coronary sinus and into a cardiac vein to position electrodes along the left ventricle (LV) for sensing LV EGM signals and delivering pacing pulses to the LV. In some examples, system 8 may be a single chamber system, or otherwise not include atrial lead 21.

In some examples, ventricular lead 20 is anchored along the right ventricular apex or the intraventricular septum by a fixation member (not shown), such as tines positioned at the distal end of lead 20 in the vicinity of electrode 22 or a helical screw, which may also serve as electrode 22. Use of a fixation member generally anchors the position of ventricular lead 20 in the RV.

Implantable medical device circuitry configured for performing the methods described herein and an associated battery or batteries are housed within a sealed housing 12. Housing 12 may be conductive so as to serve as an electrode for use as an indifferent electrode during pacing or sensing or as an active electrode during defibrillation. As such, housing 12 is also referred to herein as "housing electrode" 12. In other examples, an indifferent electrode may be separate from housing 12 and placed elsewhere on IMD 10, such as in the header.

EGM signal data, cardiac rhythm episode data, impedance and lead dislodgement data acquired by IMD 10 can be transmitted to an external device 30. External device 30 may be a computing device, e.g., used in a home, ambulatory, clinic, or hospital setting, to communicate with IMD 10 via wireless telemetry. External device 30 may be coupled to a remote patient monitoring system, such as Carelink®, available from Medtronic. External device 30 may be, as examples, a programmer, external monitor, or consumer device, e.g., smart phone.

External device 30 may be used to program commands or operating parameters into IMD 10 for controlling IMD function, e.g., when configured as a programmer for IMD 10. For example, external device 30 may program IMD 10 to take lead impedance measurements, and other biological impedance measurements, at specified intervals as well as based on triggering events. External device 30 may be used to interrogate IMD 10 to retrieve data, including device operational data as well as physiological data accumulated in IMD memory. The interrogation may be automatic, e.g., according to a schedule, or in response to a remote or local user command. Programmers, external monitors, and consumer devices are examples of external devices 30 that may be used to interrogate IMD 10. Examples of communication techniques used by IMD 10 and external device 30 include radiofrequency (RF) telemetry, which may be an RF link established via Bluetooth, WiFi, or medical implant communication service (MICS).

To measure impedance, such as lead impedance, IMD 10 may output an electrical current stimulation signal and measure a resulting induced voltage across the selected electrodes. IMD 10 may include two stimulation circuits. One stimulation circuit may be configured as a current source and the second may be configured as a below circuit ground current sink circuit. The source and sink stimulation circuits may allow the voltage at electrode interface to float with respect to the current source and sink voltage. In this manner, the lead impedance measurement circuit may reduce the measurement time because the circuit does not need to slew and settle a common node capacitance that may be connected to the two or more electrodes involved in the impedance measurement. A reduced measurement time may be desirable when inserting an impedance measurement in the few fractions of a second of the cardiac cycle available to measure lead impedance and not interfere with other measurements or therapy delivery. In this disclosure, the "electrical current stimulation signal" may induce a voltage across selected electrodes, however in the context of lead impedance measurement the electrical current stimulation signal may be configured so that the stimulation signal does not stimulate the tissue, for example, in the same manner a bradycardia pacing pulse, an ATP pulse, or a defibrillation pulse would stimulate the tissue. In some examples, a pacing pulse may cause cardiac tissue depolarization, but the lead impedance electrical current stimulation pulse may be low enough amplitude to avoid stimulating, e.g., depolarizing tissue, but high enough to induce the voltage to measure the impedance.

Lead impedance is one example of an impedance measurement performed by IMD 10. Other types of biological impedance measurements may provide information about patient breathing, water retention, cardiac contractility, respiratory effort and so on.

The stimulation portion of the impedance measurement circuit may be configured such that source and the sink current are set to the same amplitude. For example, a dual amplifier may force the current to match going into and coming out of the electrode interface, which is also connected to the patient's tissue. Sourcing the current and sinking the same current in the same direction at approximately the same time may balance the charge at the electrode-tissue interface. The accuracy of the measurement then depends on how well the source current matches the sink current. In this manner, the impedance measurement circuit of this disclosure may determine an impedance measurement with less slewing and a quick rise time, when compared to outputting a source current and grounding the electrode-tissue interface to take the impedance measurement. In addition, the source and sink current pulse may provide charge balancing. The technique itself is not limited to being just biphasic. In some examples the stimulation portion may deliver a monophasic pulse, or any other type of pulse train. A biphasic pulse may provide advantages because charge balancing on the electrode interface helps prevent corrosion on the electrodes.

The separate source and sink current circuits may provide an additional advantage in detecting an open circuit in one of the electrode pathways while taking an impedance measurement. An open circuit may be caused by a lead fracture, loose connection at the header of IMD 10, or some other cause. The impedance measurement circuitry of this disclosure may incorporate a separate monitor circuit coupled to each of source amplifier and the sink amplifier. The monitor circuit may be configured to output an indication of an error if either the source or the sink was unable to reach the correct current stimulation amplitude. In this manner, the impedance measurement circuit of this disclosure may immediately detect an open circuit on the specific source pathway or sink pathway during an impedance measurement. In some examples, the impedance measurement circuit may also detect a short circuit that prevents a signal from traveling between IMD 10 and an electrode. For example, a short circuit in between conductors of ventricular lead, or in the header of IMD 10 may shunt a sense signal or an output signal from traveling between one or more of electrodes 22, 24 or 42 and IMD 10.

The impedance measurement circuit may also warm up the measurement circuitry before taking an impedance measurement. Other types of impedance measurement circuits may use the full programmed stimulation current to warm up the current gain amplifier to the appropriate operating points by dumping the stimulation current internally onto a resistor load. Dumping current into an internal resistor load may result in amount of energy wasted during the analog warmup time. In contrast, the impedance measurement circuit of this disclosure may use a proportionally scaled down portion of the programmed stimulation current to warm up the measurement circuit. When it is time to output the stimulation current to the electrode interface, the impedance measurement circuit may switch over to the full 100% of the programmed current, output the current on the stimulation pathway, and measure the resulting induced voltage at the electrode-tissue interface.

The example of a cardiac defibrillation device in FIG. 1 is just one example application for the techniques of this disclosure. Other devices with a similar lead and electrode arrangement may also benefit from the techniques described herein. Some examples of other devices may include neurostimulators, spinal stimulators, gastric stimulators, and other types of devices. In other examples, some external or partially implanted devices may benefit from these techniques, for example, particularly wearable cardiac defibrillators, automated external defibrillators (AEDs), and external pacemakers that are connected to implanted leads for temporary pacing and other similar devices.

Figure 2:
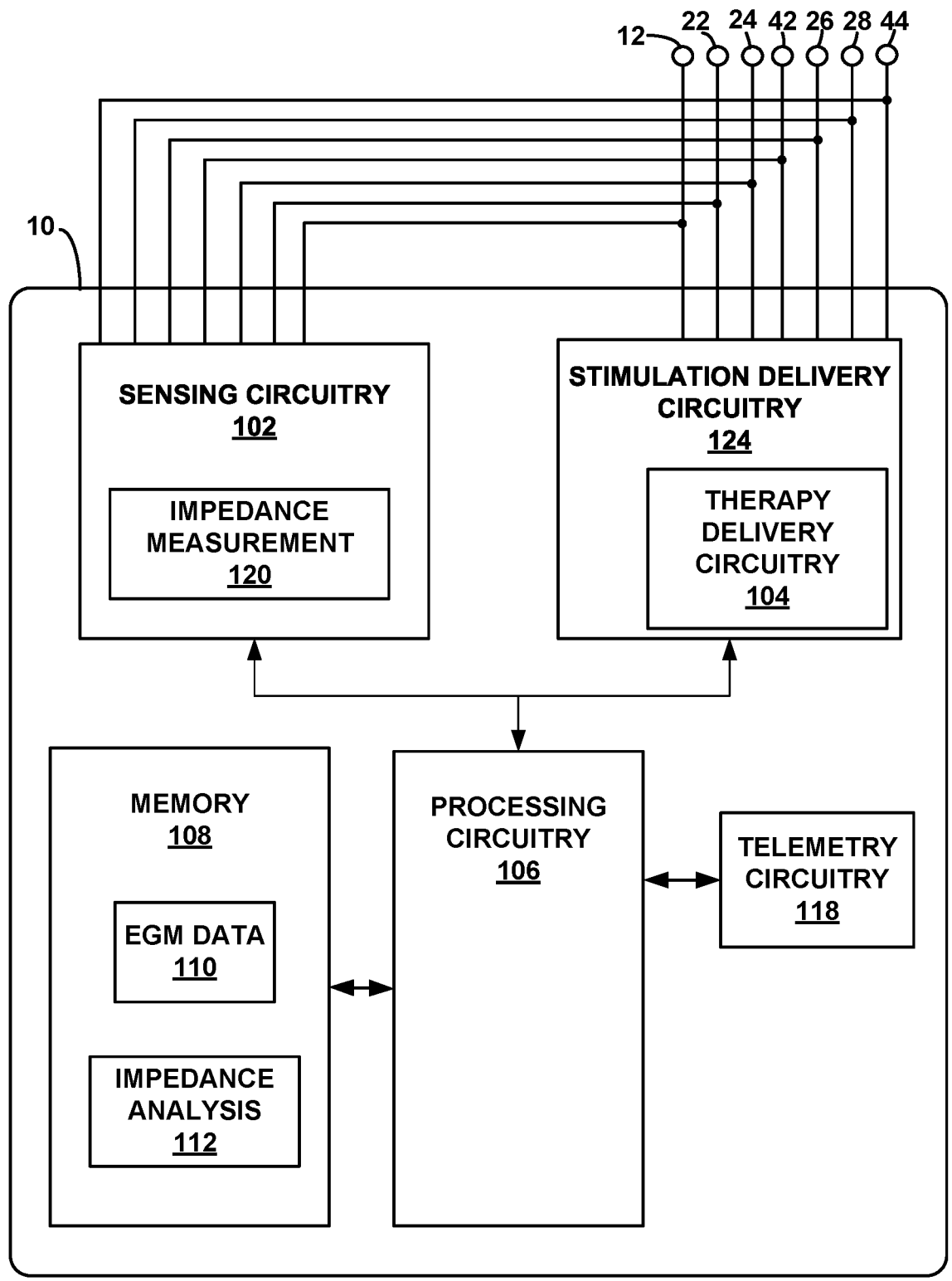
FIG. 2 is a functional block diagram of an example implantable medical device configured to measure impedance between two or more electrodes.

FIG. 2 is a functional block diagram of an example implantable medical device configured to measure impedance between two or more electrodes. In the example illustrated by FIG. 2, IMD 10 includes sensing circuitry 102, stimulation delivery circuitry 124, processing circuitry 106, associated memory 108, and telemetry circuitry 118.

Processing circuitry 106 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 108 may store program instructions, which may include one or more program modules, which are executable by processing circuitry 106. When executed by processing circuitry 106, such program instructions may cause processing circuitry 106 and IMD 10 to provide the functionality ascribed to them herein. The program instructions may be embodied in software, firmware and/or RAMware. Memory 108 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Sensing circuitry 102 may receive cardiac electrical signals from selected combinations of two or more of electrodes 22, 24, 26, 28, 42 and 44 carried by the ventricular lead 20 and atrial lead 21, along with housing electrode 12. Sensing circuitry 102 is configured to sense cardiac events attendant to the depolarization of myocardial tissue, e.g., P-waves and R-waves. Sensing circuitry 102 may include switching circuitry for selectively coupling electrodes 12, 22, 24, 26, 28, 42, 44 to sensing circuitry 102 in order to monitor electrical activity of heart 16. In other examples, not shown in FIG. 2, sensing circuitry 102 may receive cardiac electrical signals from other electrodes such as one or more LV electrodes, as described above in relation to FIG. 1. The switching circuitry may include a switch array, switch matrix, multiplexer, or any other type of switching device suitable to selectively couple one or more of the electrodes to sensing circuitry 102. In some examples, processing circuitry 106 selects the electrodes to function as sense electrodes, or the sensing vector, via the switching circuitry within sensing circuitry 102.

Sensing circuitry 102 may include impedance measurement circuitry 120 and multiple sensing channels, each of which may be selectively coupled to respective combinations of electrodes 12, 22, 24, 26, 28, 42, 44 to detect electrical activity of a particular chamber of heart 16, e.g., an atrial sensing channel and one or more ventricular sensing channels. Each sensing channel may be configured to amplify, filter, and rectify the cardiac electrical signal received from selected electrodes coupled to the respective sensing channel to detect cardiac events, e.g., P-waves and/or R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter.

Sensing circuitry 102 outputs an indication to processing circuitry 106 in response to sensing of a cardiac event, in the respective chamber of heart 16 (e.g., detected P-waves or R-waves or measured impedance). In this manner, processing circuitry 106 may receive detected cardiac event signals corresponding to the occurrence of detected R-waves and P-waves in the respective chambers of heart 16. Indications of detected R-waves and P-waves may be used for detecting ventricular and/or atrial tachyarrhythmia episodes, e.g., ventricular, or atrial fibrillation episodes. Sensing circuitry 102 may also pass one or more digitized EGM signals to processing circuitry 106 for analysis, e.g., for use in cardiac rhythm discrimination. Processing circuitry 106 may use the indications of R-waves and/or the digitized ventricular EGM signals to detect dislodgement of ventricular lead 20 according to the techniques described herein. Indications of R-wave and P-wave timing, as well as digitized EGMs, may be stored in memory 108 as EGM data 110.

Memory 108 may also store impedance analysis module 112. Impedance analysis module 112 may be a software, firmware, or RAMware module executable by processing circuitry 106 to cause processing circuitry 106 to provide functionality related to operating stimulation deliver circuitry 124 and impedance measurement circuits 120. For example, processing circuitry 106 may retrieve settings from memory 108 to determine which electrodes to select to determine impedance measurements. Processing circuitry may store the results of an impedance measurement at a location in memory 108, e.g., within impedance analysis module 112. Processing circuitry 106 may load impedance analysis module 112 from memory 108 and execute the loaded impedance analysis module 112 in response to an event, based on a command from external device 30 received via telemetry circuitry 118, and so on. In other examples, processing circuitry 106 may execute impedance analysis module 112 periodically, e.g., according to a schedule, or substantially continuously, throughout the operation of IMD 10.

Processing circuitry 106 may control stimulation delivery circuitry 124 to connect a current source to a first electrode, or electrodes, and a current sink to a second electrode, or electrodes. Stimulation delivery circuitry 124 may include switches, amplifiers, filter circuits, power supplies, and so on configured to generate and route the electrical current pulse to the selected electrodes. In some examples, a switches may comprise a transistor. In some examples, stimulation delivery circuitry 124 may include switching circuitry configured to output the source stimulation current to a first electrode of the plurality of electrodes 12-44. Stimulation delivery circuitry 124 may output the sink stimulation current to a second electrode of the plurality of electrodes. Impedance measurement circuitry 120 of sensing circuitry 102 may measure the induced voltage, for example, between a third electrode and a fourth electrode of the plurality of electrodes. In some examples, the impedance measurement may be described as a four-wire measurement. In other examples, stimulation generation circuitry 124 may output the source stimulation current to two or more electrodes and sink the return current through a single electrode, and vice versa. In other examples, stimulation generation circuitry 124 may output the source stimulation current to two or more electrodes and sink the return current through two or more different electrodes.

In some examples, processing circuitry 106 may respond to an impedance measurement out of range by generating a user alert, such as a patient or clinician alert, which may be transmitted by telemetry circuitry 118 or by logging the impedance measurement at a memory location for a later telemetry session, e.g., with external device 30 described above in relation to FIG. 1. Telemetry circuitry 118 is used to communicate with external device 30, for transmitting data accumulated by IMD 10 and for receiving interrogation and programming commands from external device 30. In other examples, IMD 10 may be configured to automatically, or in response to a command from external device 30, select a new sensing or stimulation electrode vector and/or disable a particular therapy. In some examples, IMD 10 may be configured to change a sensing or stimulation vector from a vector that has developed a high impedance, or an open, to a different vector that is within a predetermined impedance range. In other words, IMD 10 may be configured to automatically change from a first electrode vector to a second electrode vector based on the measured voltage induced by the stimulation current.

Impedance measurement circuitry 120 may also include a first monitoring circuit, e.g., connected to the current source, which may be configured to determine whether the output source current reaches the expected current stimulation amplitude. For example, the monitor circuit may measure a voltage, and based on the measured voltage provide an estimate of the output current. In response to determining that the measured voltage satisfies a voltage threshold, the monitor circuit may output an indication that the voltage satisfied the threshold e.g., by outputting a logical HIGH or LOW to processing circuitry 106. In some examples, to satisfy the threshold means the measured voltage is greater than the threshold. In other examples, to satisfy the threshold may mean the measured voltage is less than the threshold or within a voltage range of the threshold. Impedance measurement circuitry 120 may also include a second monitoring circuit, e.g., connected to the current sink, which may perform a similar function.

Processing circuitry 106 may control therapy delivery circuitry 104 to deliver electrical therapy, e.g., cardiac pacing, anti-tachyarrhythmia therapy, cardiac resynchronization therapy, or cardioversion or defibrillation shock pulses, to heart 16 according to therapy parameters stored in memory 108. Therapy delivery circuitry 104 is electrically coupled to electrodes 12, 22, 24, 26, 28, 42, 44, and is configured to generate and deliver electrical therapy to heart 16 via selected combinations of electrodes 12, 22, 24, 26, 28, 42, 44. Therapy delivery circuit 104 may include charging circuitry, one or more charge storage devices, such as one or more high voltage capacitors and/or one or more low voltage capacitors, and switching circuitry that controls when the capacitor(s) are discharged to selected combinations of electrodes 12, 22, 24, 26, 28, 42, 44. Charging of capacitors to a programmed pulse amplitude and discharging of the capacitors for a programmed pulse width may be performed by therapy delivery circuit 104 according to control signals received from processing circuitry 106.

Memory 108 may store time intervals, counters, or other data used by processing circuitry 106 to control the delivery of pacing pulses by therapy delivery circuitry 104. Such data may include intervals and counters used by processing circuitry 106 to control the delivery of pacing pulses to heart 16. The intervals and/or counters are, in some examples, used by processing circuitry 106 to control the timing of delivery of pacing pulses relative to an intrinsic or paced event in another chamber. Memory 108 also stores intervals for controlling cardiac sensing functions such as blanking intervals and refractory sensing intervals and counters for counting sensed events for detecting cardiac rhythm episodes. Events sensed by sense amplifiers included in sensing circuitry 102 are identified in part based on their occurrence outside a blanking interval and inside or outside of a refractory sensing interval. Events that occur within predetermined interval ranges are counted for detecting cardiac rhythms.

Figure 3:
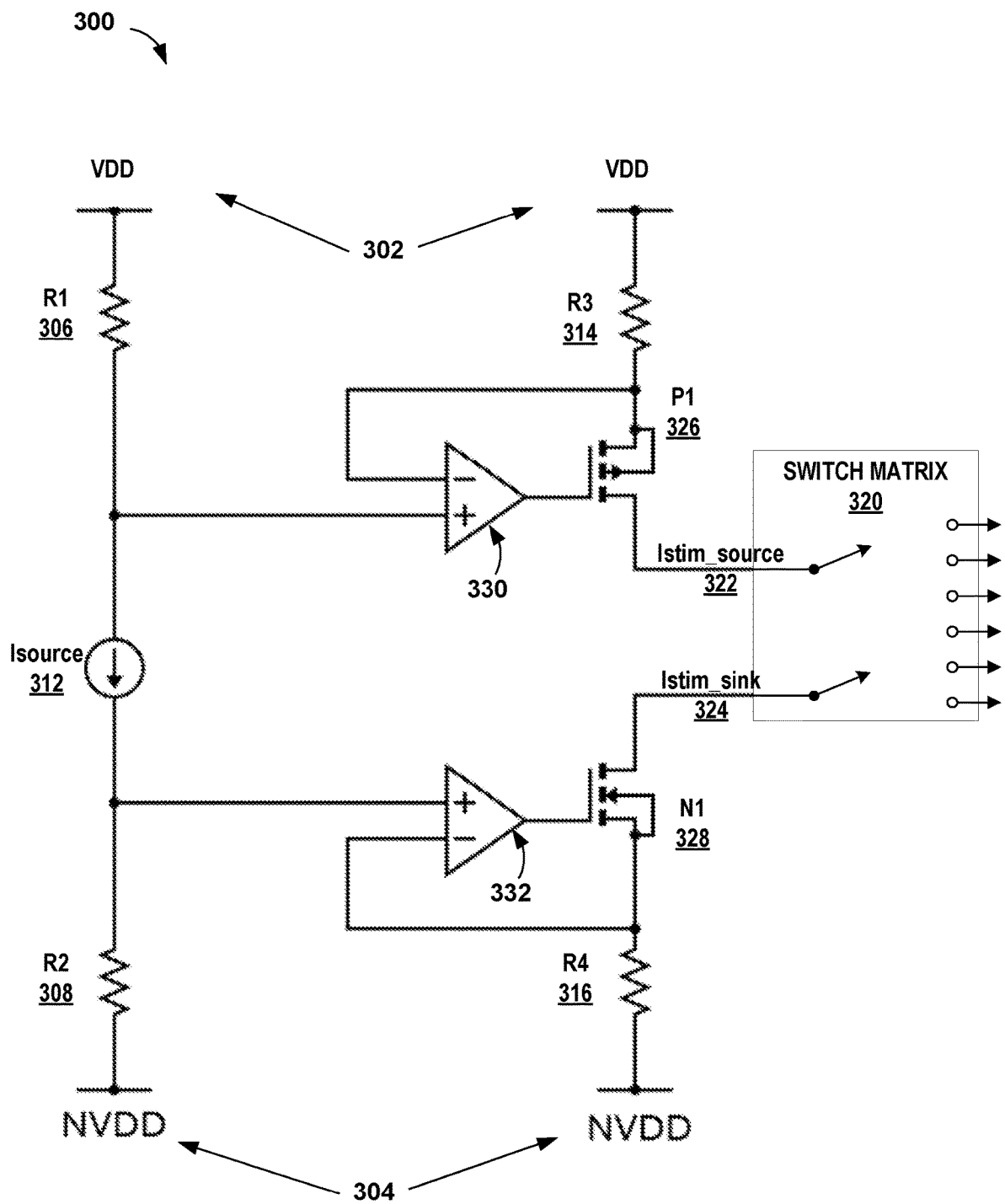
FIG. 3 is a schematic diagram illustrating one possible implementation of the current pulse stimulation circuit of this disclosure.

FIG. 3 is a schematic diagram illustrating one possible implementation of the current pulse stimulation circuit of this disclosure. Circuit 300 may be an example implementation of a portion of stimulation generation circuitry 124 described above in relation to FIG. 2.

Circuit 300 may include a source stimulation circuit that includes a first switch P1 326 configured to control a source stimulation current, Istim_source 322. Amplifier 330 drives a control terminal of switch P1 326, which in the example of circuit 300 is a P-type metal oxide semiconductor field effect transistor (MOSFET). Circuit 300 also includes a sink stimulation circuit with a second switch, N1 328 configured to control sink stimulation current Istim_sink 324. Amplifier 332 drives a control terminal of the switch N1 328, which is an N-type MOSFET in the example of circuit 300. In other examples switch P1 326 and N1 328 may be other types of switches, such as bipolar junction transistors (BJT), insulated gate BJT (IGBT), and so on.

Reference current, Isource 312 is coupled to both the source stimulation circuit and the sink stimulation circuit. Isource 312 connects to the non-inverting terminal of amplifier 330 and the non-inverting terminal of amplifier 332 such that a magnitude of source stimulation current Istim_source 322 approximately equals a magnitude of sink stimulation current Istim_sink 324. In this disclosure, approximately equal, or approximately the same means and equal time or of equal value within manufacturing and measurement tolerances.

In more detail, power supply Vdd 302 connects to a first terminal of resistor R1 306, a second terminal of R1 306 connects to Isource 312 and the non-inverting terminal of amplifier 330. Negative power supply NVdd 304 connects to Isource 312 and to the non-inverting terminal of amplifier 332 through resistor R2 308. Vdd 302 also connects to the source of MOSFET P1 326 and to the inverting terminal of amplifier 330 through resistor R3 314. The output of amplifier 330 connects to the gate of P1 326. The drain of P1 326 is the output of the source stimulation circuit and provides Istim_source 322 to switch matrix 320. Switch matrix 320 is configured to output Istim_source 322 and Istim_sink 324 to any of the plurality of electrodes, e.g., electrodes 12-44 described above in relation to FIG. 2.

Negative power supply NVdd 304, e.g., the negative voltage reference, is level shifted compared to the voltage of power supply Vdd 302 to be below ground. Therefore, the return electrode connected to Istim_sink 324 by switch matrix 320 is below the circuit ground of circuit 300. Power supply NVdd 304 connects to the source of MOSFET N1 328 and to the inverting terminal of amplifier 332 through resistor R4 316. The output of amplifier 332 connects to the gate of N1 328. The output of the sink stimulation circuit is the drain of N1 328, which provided Istim_sink 324 to switch matrix 320.

Described another way, the source stimulation circuit receives power from a power supply Vdd 302 while the sink stimulation circuit receives power from power supply NVdd 304. The voltage of the NVdd 304 is level shifted such that, with respect to a ground reference voltage of circuit 300, the voltage of the NVdd 304 is opposite in polarity to Vdd 302 and approximately equal to the voltage of Vdd 302. In operation, the output terminal of the source stimulation circuit, e.g., the drain of P1 326, is configured to couple to tissue of a patient by connecting via switch matrix 320 to an electrode on a lead, such as leads 20 and 21 described above in relation to FIG. 1. The output terminal of the sink stimulation circuit, e.g., N1 328 is also configured to couple to the tissue of the patient in a similar manner as the source stimulation circuit. During an impedance measurement, the source stimulation current and the sink stimulation current may induce a voltage at the tissue of the patient. In some examples, the same set of electrodes, or a different set of electrodes than those used to output and return the current pulse may couple the voltage to impedance measurement circuit 120 described above in relation to FIG. 2. Processing circuitry 106 may receive an indication of the measured impedance and record the measured impedance at memory 108. Processing circuitry 106 may also take other actions based on the value of the measured lead impedance, such as schedule another lead impedance measurement, or some other action as described above in relation to FIGS. 1 and 2.

Figure 4:
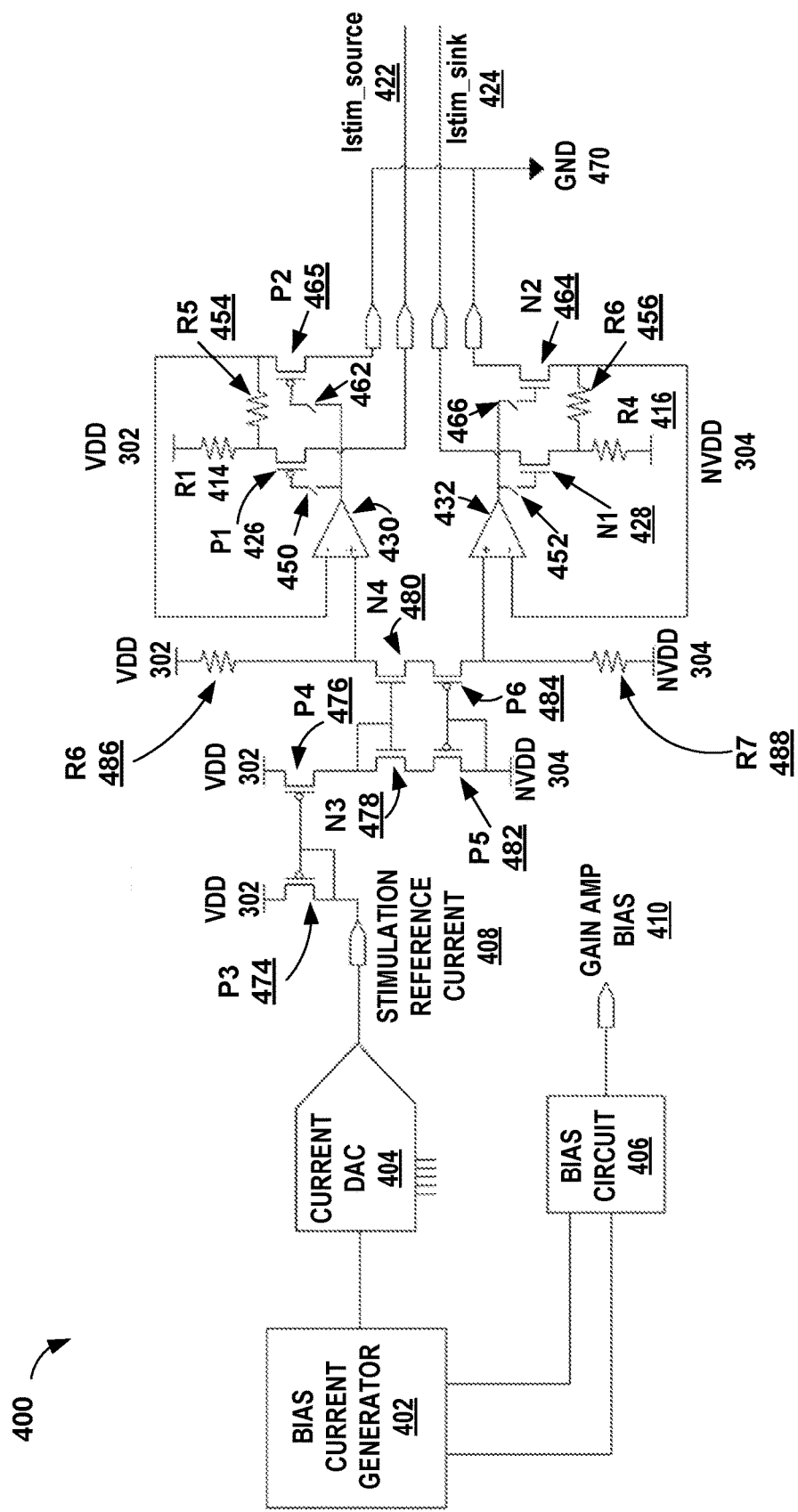
FIG. 4 is a schematic diagram illustrating a possible implementation of the current pulse stimulation circuit used to measure impedance.

FIG. 4 is a schematic diagram illustrating a possible implementation of the current pulse stimulation circuit that may be used to measure impedance. Circuit 400 is an example implementation of circuit 300 described above in relation to FIG. 3 and may have the same or similar functions and characteristics.

The example of circuit 400 includes power supply Vdd 302 and negative power supply Nvdd 304, which is level shifted to be below circuit ground, as described above in relation to FIG. 3. The reference current, e.g., reference current 312 described above in relation to FIG. 3, is implemented as a current mirror including transistors N3 478, N4 480, P5 482 and P6 484 in circuit 400. Similar to circuit 300, a non-inverting terminal of amplifier 430 connects to the voltage reference created by the IR drop from the mirrored reference current and R6 486 and the non-inverting terminal of amplifier 432 connects to a second voltage reference created by the IR drop above the negative supply from the mirrored reference current and R7 488. In other words, the reference current is coupled to both the source stimulation circuit and the sink stimulation circuit such that a magnitude of source stimulation current Istim_source 422 approximately equals a magnitude of sink stimulation current Istim_sink 424.

Similar to circuit 300, in circuit 400 power supply Vdd 302 connects to the non-inverting terminal of amplifier 330, as well as the reference current, e.g., the drain terminal of N4 480, through resistor R6 486. Negative power supply NVdd 304 connects to the reference current, e.g., to the drain terminal of P6 484, as well as the non-inverting terminal of amplifier 432 through resistor R7 488. The source terminal of N4 480 connects to the source terminal of P6 484. The gate of N4 480 connects to the gate of N3 478 and to the drain terminal of N3 478. The gate of P6 484 connects to the gate of P5 482 and to the drain terminal of P5 482 as well as NVdd 304.

Vdd 302 also connects through resistor R1 414 to the source terminal of source stimulation current switch, transistor P1 426. The drain of P1 426 is the output of the source stimulation circuit and provides Istim_source 422 to the selected electrode or electrodes. The output of amplifier 330 connects to the gate of P1 426 through switch 450 and to the gate of P2 465 through switch 462. Processing circuitry, e.g., processing circuitry 106 described above in relation to FIG. 2, may directly or indirectly control the operation of switches 450, 462, 452 and 466 for warm-up and delivery of the stimulation current pulse during an impedance measurement. In addition, the processing circuitry may use switches 450, 462, 452 and 466, or similar switches, to enable or disable the source stimulation circuit or the sink stimulation circuit.

The inverting terminal of amplifier 430 connects to transistor P2 465. Warm-up resistor R5 454 connects the source terminal of P2 465 to the source terminal of P1 426. Vdd 302 connects to the source terminal of P1 426 through resistor R1 414. The drain of warm-up switch P2 465 connects to ground 470.

As described above in relation to FIG. 3, negative power supply NVdd 304, e.g., the negative voltage reference, is level shifted compared to the voltage of power supply Vdd 302 to be below ground. Power supply NVdd 304 connects to the source of transistor N1 428 through resistor R4 416. Warm-up resistor R6 456 connects the source terminal of N1 428 to the source terminal of transistor N2 464. The output of amplifier 432 connects to the gate of N1 428 through switch 452 and to the gate of N2 464 through switch 466. The output of the sink stimulation circuit is the drain of N1 428, which provided Istim_sink 424 to the selected electrode or electrodes. The source terminal of N2 464 connects to the inverting terminal of amplifier 432. The drain of warm-up switch N2 464 connects to ground 470.

Circuit 400 provides stimulation reference current 408 to a second current mirror that includes transistors P3 474 and P4 476. Current digital to analog converter (DAC) 404 outputs stimulation reference current 408 to drain and the gates of P3 474 and P4 476. Vdd 302 connects to the source terminals of P3 474 and P4 476. The drain of P4 476 connects to the gates of N3 478 and N4 480, as well as the drain terminal of N3 478. Bias current generator 402 outputs a signal to current DAC 404 and to bias circuit 406. The output of bias circuit 406 connects to gain amp bias 410.

In operation, the warm-up circuit, e.g., transistor P2 465 and resistor R5 454 for the source stimulation circuit, is configured to carry a warm-up current at a first time, before delivering the full source stimulation current Istim_source 422. Amplifier 430 may drive the gate, e.g., the control terminal, of switch P1 426 to output Istim_source 422 at a second time, subsequent to the first time. The warm-up current carried by P2 465 to ground 470 may be set as a predetermined portion of the source stimulation current. In some examples, the magnitude of the warm-up current may be a fraction of the full source stimulation current Istim_source 422, e.g., less than one-tenth of Istim_source 422. In some examples the warm-up current may be approximately one-twentieth, one-fiftieth, or some other portion of Istim_source 422.

The warm-up circuit for the sink stimulation current may operate in a similar manner to the source stimulation current. That is, the warm-up circuit, e.g., transistor N2 464 and resistor R6 456, for the source stimulation circuit, is configured to carry a warm-up current at a first time, before receiving the full sink stimulation current Istim_sink 424. Amplifier 432 may drive the gate of switch N1 428 to output Istim_sink 424 at a second time, subsequent to the first time. The warm-up current conducted by N2 464 to ground 470 may be set as a predetermined portion of the source stimulation current. In this manner, the impedance measurement circuit of this disclosure may provide an energy savings advantage when compared to other examples of warm-up circuits that use the full stimulation current. Reducing the electrical energy used during warm-up of the impedance measurement circuit may result in longer battery life for battery operated devices that include the impedance measurement circuit. Longer battery life may result in improved patient outcomes because a longer battery life may mean fewer surgeries and risk of infection to replace a depleted 1 MB. In the example of rechargeable IMDs, a longer battery life may mean less patient time spent recharging the 1 MB.

Figure 5:
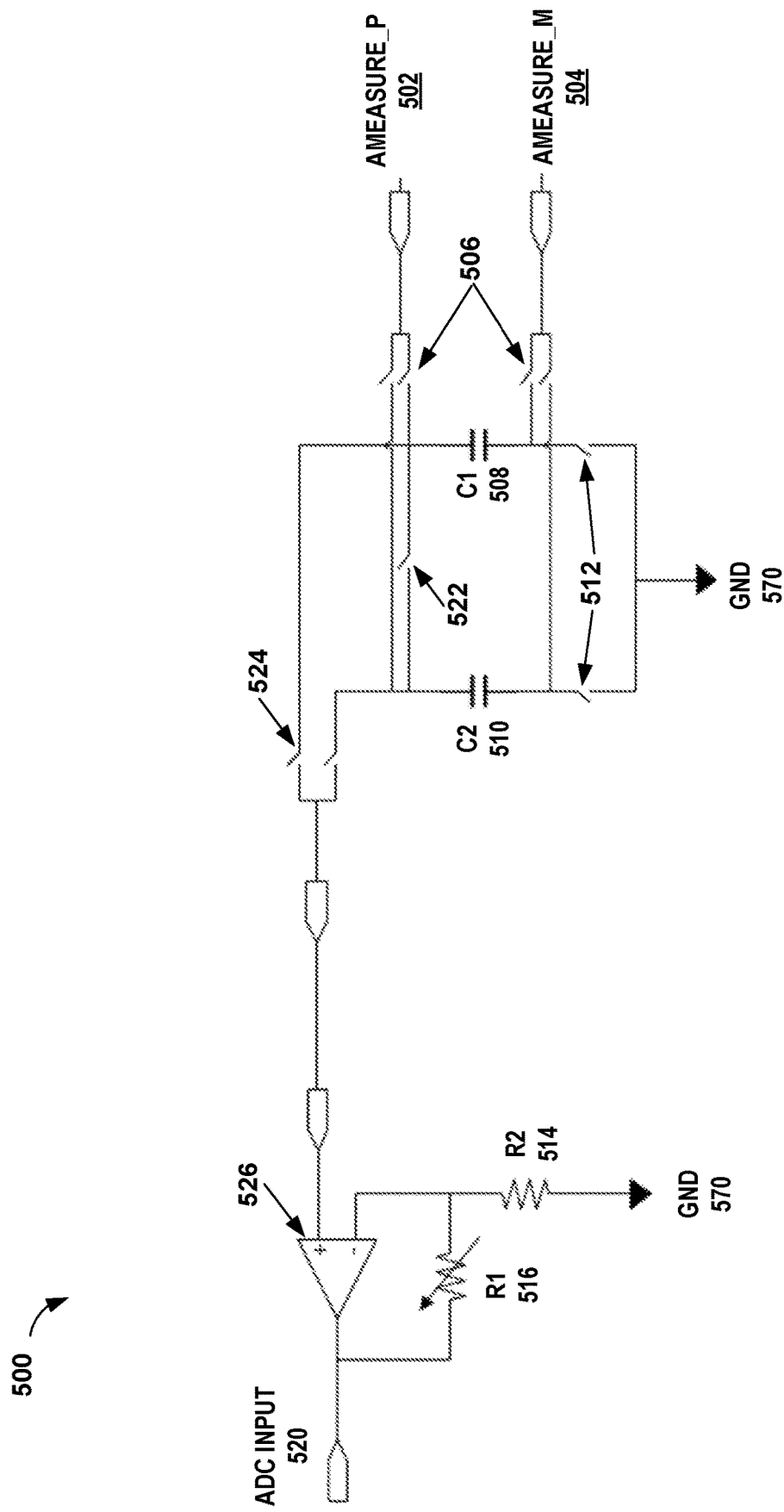
FIG. 5 is a schematic diagram illustrating an example sample and measurement circuit for measuring impedance, according to one or more techniques of this disclosure.

FIG. 5 is a schematic diagram illustrating an example sample and measurement circuit for measuring impedance, according to one or more techniques of this disclosure. Circuit 500 is one example implementation of impedance measurement circuit 120 described above in relation to FIG. 2 that may be used along with stimulation circuits 300 and 400 described above in relation to FIGS. 3 and 4.

A switch matrix, such as switch matrix 320 described above in relation to FIG. 3, may connect source measure terminal AMeasure_P 502 and return measure terminal AMeasure_M 504 to any electrode, or electrodes. Circuit 500 may sample the induced voltage at AMeasure_P 502 and AMeasure_M 504 that result from the output source stimulation current and sink stimulation current e.g., Istim_source 422 and Istim_sink 424 depicted in FIG. 4. Using switches 506, 522, 512 and 524 and capacitors C1 508 and C2 510, circuit 500 may sample and hold the measured voltage and output the voltage to amplifier 526. Resistors R1 516 and R2 514 may set the gain of amplifier 526, which outputs the sampled voltage to analog to digital converter (ADC) input 520. In some examples, ADC input 520 is a component of sensing circuitry 102, which outputs the sampled voltage to processing circuitry 106, as described above in relation to FIG. 2. Processing circuitry 106 may determine the impedance, such as lead impedance, based on the sampled voltage and known stimulation current.

Figure 6:
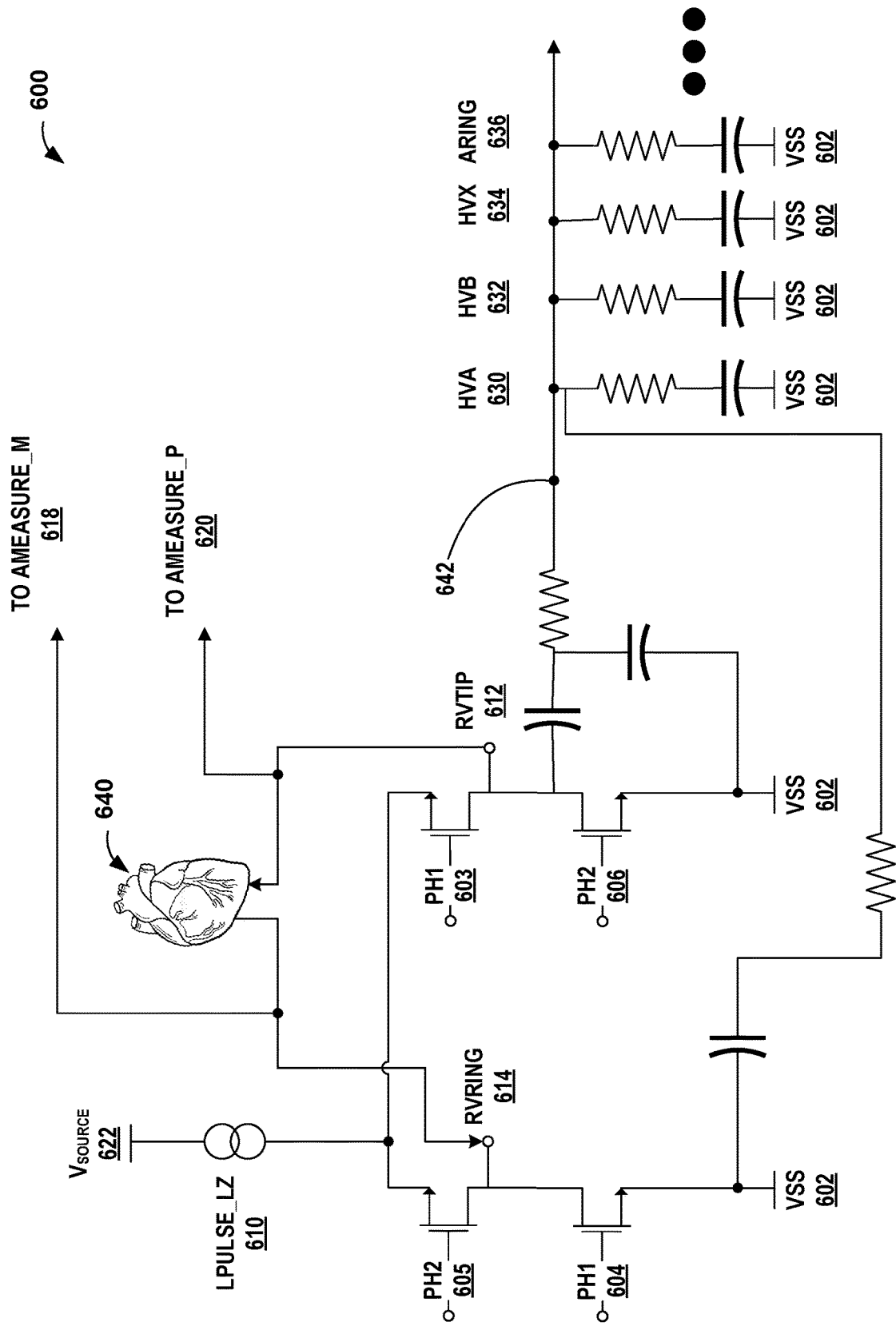
FIG. 6 is a conceptual and schematic diagram illustrating an example lead interface connected to a patient's tissue.

FIG. 6 is a conceptual and schematic diagram illustrating an example lead interface connected to a patient's tissue. The impedance measurement illustrated by circuit 600 is an example of sending a biphasic stimulation pulse to two electrodes and measuring the induced voltage on the electrodes while providing a connection to ground for the electrode interface. The techniques of this disclosure, e.g., using a separate source stimulation circuit and a sink stimulation circuit may have advantages over circuit 600.

In the example of circuit 600, a switch matrix (not shown in FIG. 6) connected AMeasure_P 620 to RVtip electrode 612 and AMeasure_M 618 to RVring electrode 614. The same or similar measurement circuit described above in relation to FIG. 5 may be used for both the technique shown in FIG. 6 as well as the techniques of this disclosure described above in relation to FIGS. 1-4.

RVtip 612 and RVring 614 are also connected to the rest of the electrode interface, which in the example of FIG. 6 includes HVA 630, HVB 632, HVX 634, Aring 636 and so on. Each type of cardiac device may have a different electrode interface. For example, a single lead pacing device may only have RVtip 612 and RVring 614, or alternatively Atip (not shown in FIG. 6) and Aring 636. In other examples, an implantable defibrillator may include defibrillation therapy electrodes and a cardiac resynchronization therapy device may also include electrodes in contact with the left ventricle of heart 640. The electrode interface, also referred to as the electrode-tissue interface or the star node 642 in this disclosure, may include common mode capacitance connected in some examples to ground or to the case node. For example, as shown in circuit 600 each of RVring 614, RVtip 612, HVA 630 and so on connects to Vss 602 through a resistor and/or a capacitor.

A processor for a device using lead impedance measurement circuit of FIG. 6 compensates for the common mode capacitance on the electrode interface, which may be caused by channel capacitors, filter feed through capacitors, delivery circuit, blocking FETs, and other components that may not be shown in FIG. 6. Circuit 600 may output a biphasic current stimulation from LPulse_LZ 610 by first closing switches PH1 603 and PH1 604 for the first phase, then closing switches PH2 605 and PH2 606 for the second phase. The biphasic pulse may be output in the same timing window for charge balancing, as described above in relation to FIG. 1. Circuit 600 may then measure the induced voltage across the selected electrodes, e.g., via AMeasure_M 618 and AMeasure_P 620 to determine the impedance. Because of short stimulation pulse width and capacitance connected to star node 642, the time constant for the induced voltage to reach a DC steady state solution may be long. The measurement circuit may measure the induced voltage as the voltage changes, e.g., before reaching steady state, which may result in the final voltage measurement being inaccurate. To get around this issue, devices that use circuit 600 may compensate by adding additional measurements and calculations, which may be complex and firmware intensive. For example, a device may implement a stimulation difference measurement where the device may execute two current stimulations with different current amplitudes in an attempt to measure the time constants and extract the impedance that would result in that time constant.

To measure lead impedance with circuit 600, each device configuration, e.g., single channel, dual channel, heart failure devices that include RA, RV and LV leads, may have a different configuration and a different lead impedance calculation. Each configuration may have separate calibration constants stored at a memory of the device to perform the complex firmware calculations to determine the lead impedance. Because of manufacturing variation, calibration constants may be determined during manufacturing testing for each individual device and stored in that device's memory. For example, RVtip 612 may be a smaller electrode and therefore have higher impedance compared to the RVRing 614 electrode.

In contrast, the techniques of this disclosure, described above in relation to FIGS. 1-4, use separate source stimulation circuit and the sink stimulation circuit, and allow the voltage at star node 642 to float with respect to the current source and sink voltage. Unlike circuit 600, the techniques of this disclosure do not ground one of the electrodes during the impedance measurement. Because the accuracy of the measurement may depend on how well the source current matches the sink current, a current source is coupled to both the source stimulation circuit and the sink stimulation circuit, such that a magnitude of the source stimulation current approximately equals a magnitude of the sink stimulation current, which also balances the charge at the electrode-tissue interface. In this manner, the techniques of this disclosure no longer need to slew and settle the common node capacitance on the two electrodes involved in the measurement.

An advantage of the dual current source and sink stimulation architecture of this disclosure means the induced voltage may reach a steady state value within a short period when compared to circuit 600. For example, within a period of less than 100 microseconds (μs). In addition, the techniques of this disclosure may provide a higher degree of measurement accuracy with reduced FW burden and complexity, when compared to circuit 600. This may reduce cost and improve reliability of implantable medical devices. For example, for every new IMD platform, the design burden to determine the impedance measurement compensation may be reduced, when compared to development and test burden costs of an IMD platform using circuit 600. In addition, reducing the complexity, burden, and processing on time of the CPU may result in reduced electrical energy consumption and a longevity improvement for the IMD. The techniques of this disclosure may also reduce development and maintenance costs of the lead impedance feature from a productions test, FW test, and device test perspective.

In some examples, the circuit of this disclosure may include a disable circuit, e.g., switches 450, 462, 452 and 466 configured to disable the source or the sink stimulation circuit. The disable circuit may be desirable when an IMD of this disclosure may want to take an impedance measurement using the techniques of circuit 600. In this manner, the circuits of this disclosure may provide backward compatibility with other systems.

Figure 7:
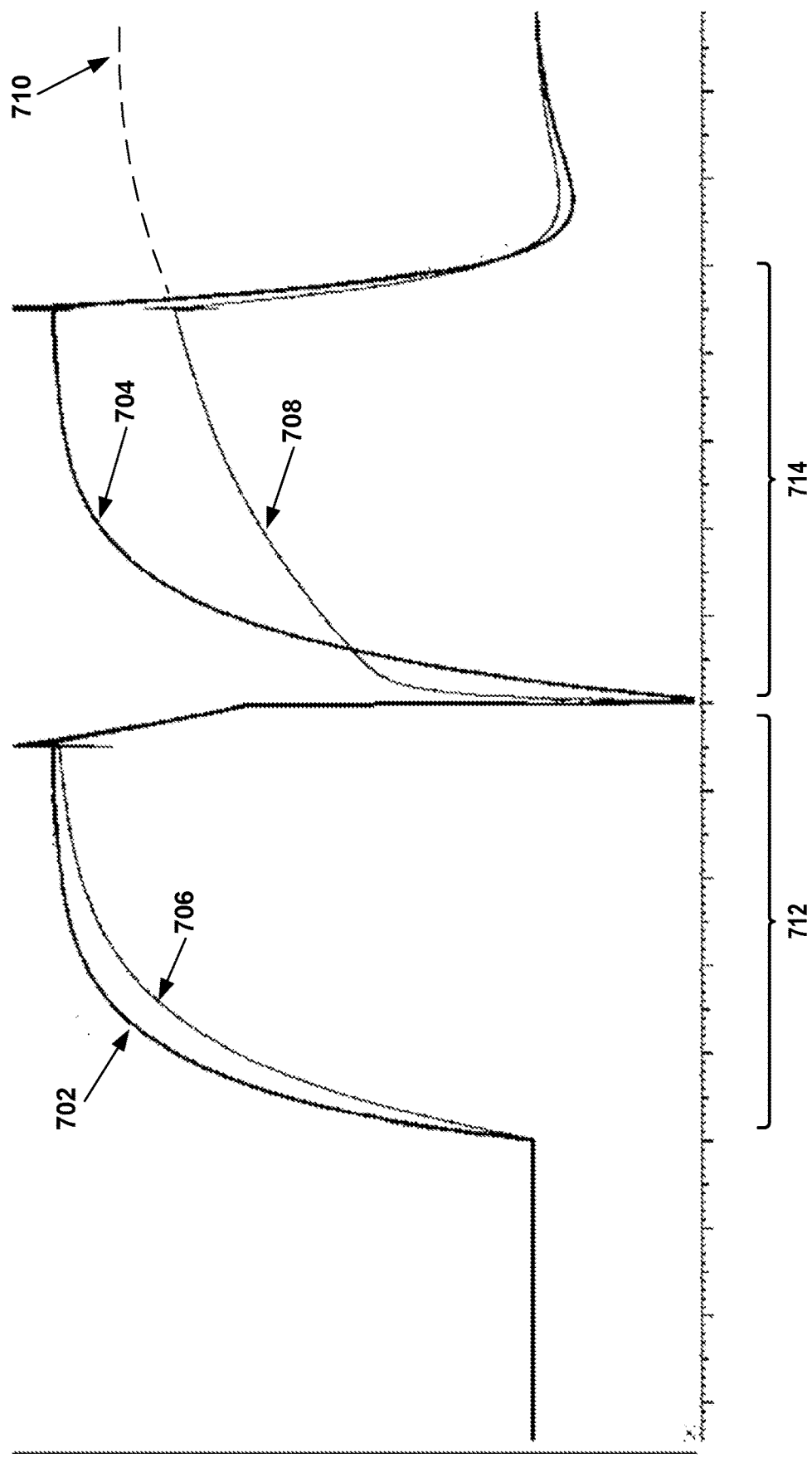
FIG. 7 is a timing diagram illustrating a comparison between the voltage settling time of different lead impedance measurement techniques.

FIG. 7 is a timing diagram illustrating a comparison between different lead impedance measurement techniques. The curves shown by 702 and 704 illustrate the induced voltage caused by current source stimulation current (702) and the sink stimulation current (704). The induced voltage may reach a steady state within the time windows depicted by 712 and 714. In contrast the curves shown by 706 and 708, which depict the performance of circuit 600 of FIG. 6, may not reach steady state within the time windows. A short time window for an impedance measurement may be desirable when inserting an impedance measurement in the few fractions of a second of the cardiac cycle available to not interfere with other measurements or therapy delivery. In the example of FIG. 7, the second phase 708 may not reach steady state until the point indicated by 710. Lead impedance measurement techniques using the techniques that result in signals 706 and 708 may use complex testing, calibration, and firmware calculations to compensate for the long time constant caused by capacitance on the star node, as described above in relation to FIG. 6.

Figure 8:
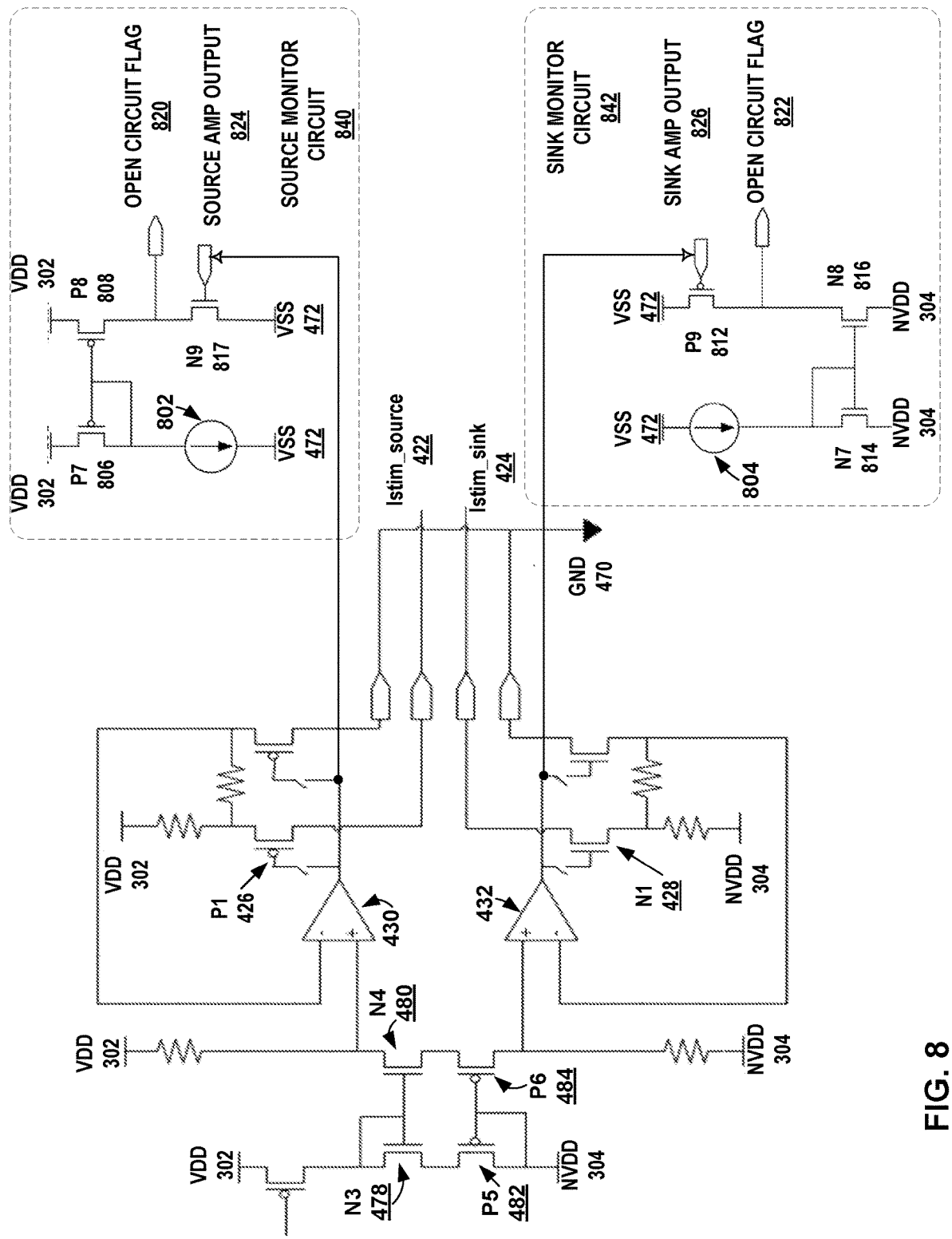
FIG. 8 is a schematic diagram illustrating an example implementation of a monitor circuit for each of the current source stimulation circuit and sink stimulation circuit, according to one or more techniques of this disclosure.

FIG. 8 is a schematic diagram illustrating an example implementation of a monitor circuit for each of the current source stimulation circuit and sink stimulation circuit, according to one or more techniques of this disclosure. The circuit in the example of FIG. 8 is an example of stimulation circuitry 124, and circuits 300 and 400 described above in relation to FIGS. 1, 3 and 4. Items in FIG. 8 with the same references numbers as items described above in relation to FIGS. 1, 3 and 4 have the same functions and characteristics as described above. FIG. 8 includes a current source, depicted by transistors N3 478, N4 480, P5 482 and P6 484 connected to a current source stimulation circuit and sink stimulation circuit.

Source monitor circuit 840 is implemented as a comparator circuit. Vdd 302 connects to the source terminal of P-type transistors P7 806 and P8 808. The gates of P7 806 and P8 808 are connected together to the drain of P7 806 and a first terminal of current source 802. A second terminal of current source 802 connects to Vss 472. The drain of P8 808 connects to Vss 472 through transistor N9 817. The output of amplifier 430 connects to source amplifier output terminal 824, which is the gate of N9 817. In operation, source monitor circuit 840 may output open circuit flag 820, e.g., to processing circuitry 106 of FIG. 1, when the voltage of the output of amplifier 430, connected to the control terminal of the switch P1 426, satisfies a threshold. In the example of FIG. 8, when the voltage output by amplifier 430 exceeds the voltage threshold, open circuit flag 820 may output a logical ZERO. When the output of amplifier 430 is less than the predetermined voltage threshold, e.g., satisfies the threshold, open circuit flag 820 may output a logical ONE, which is an indication that the voltage satisfied the threshold. In some examples, ground 470 may be connected to Vss 472. In other examples, ground 470 may be isolated from Vss 472.

Sink monitor circuit 842 is also implemented as a comparator circuit. NVdd 304 connects to the source terminal of N-type transistors N7 814 and N8 816. The gates of N7 814 and N8 816 are connected together to the drain of N7 814 and a first terminal of current source 804. A second terminal of current source 804 connects to Vss 472. The drain of N8 816 connects to Vss 472 through transistor P9 812. The output of amplifier 432 connects to sink amplifier output terminal 826, which is the gate of P9 812. In operation, sink monitor circuit 842 may output open circuit flag 822 when the magnitude of the voltage of the output of amplifier 432, connected to the control terminal of the switch N1 426, satisfies a threshold. In the example of FIG. 8, when the voltage output by amplifier 432 is more negative, e.g., less than the voltage threshold, open circuit flag 822 may output a logical ZERO. Said another way, when the magnitude of voltage at the output of amplifier 432 is less than the predetermined voltage threshold, i.e., less negative than the voltage threshold, e.g., greater than the threshold, open circuit flag 822 may output a logical ONE, which is an indication that the voltage satisfied the threshold.

In other words, the analog comparator monitors circuits of FIG. 8 monitor the output voltage of the amplifier driving the gates of the switches. When the amplifier output satisfies a threshold that indicates that the output impedance is too high, the monitor circuit may output a flag to indicate high impedance or open circuit lead, which may indicate a lead fracture or similar lead issue, as described above in relation to FIG. 1. In some examples the predetermined threshold may be set near the saturation point of the amplifier, e.g., the amplifier cannot drive the voltage magnitude higher. In other words, the amplifier is not able to drive the switch to reach the programmed stimulation current magnitude. The monitor circuits inside of the two current gain amplifiers monitor each separate amplifier and will signal to the IMD digital hardware if the current amplifier was not able to achieve the correct current output onto the electrode interface. With the separate monitor circuits, as well as with an independent current source on each electrode in the stimulation pathway, processing circuitry of the IMD may identify which electrode is an open circuit in a single impedance measurement. The open circuit flag may trigger the open circuit alert, even without the ADC input, e.g., ADC input 520, interpreting and determining the measured lead impedance.

The monitor circuits of this disclosure may provide advantages over other techniques of detecting an open circuit to an electrode. In an IMD, the pacing and sensing circuits may depend on the fact that the sensing and therapy pathways have good electrical connections and are still intact. An IMD may include algorithms running internally to ensure that the IMD is not making decisions based on noise/false senses from a broken lead as well as are not delivering therapy along a broken pathway. The monitor circuits of this disclosure may provide a rapid and accurate determination of whether or not the pathway to an electrode is intact.

Figure 9:
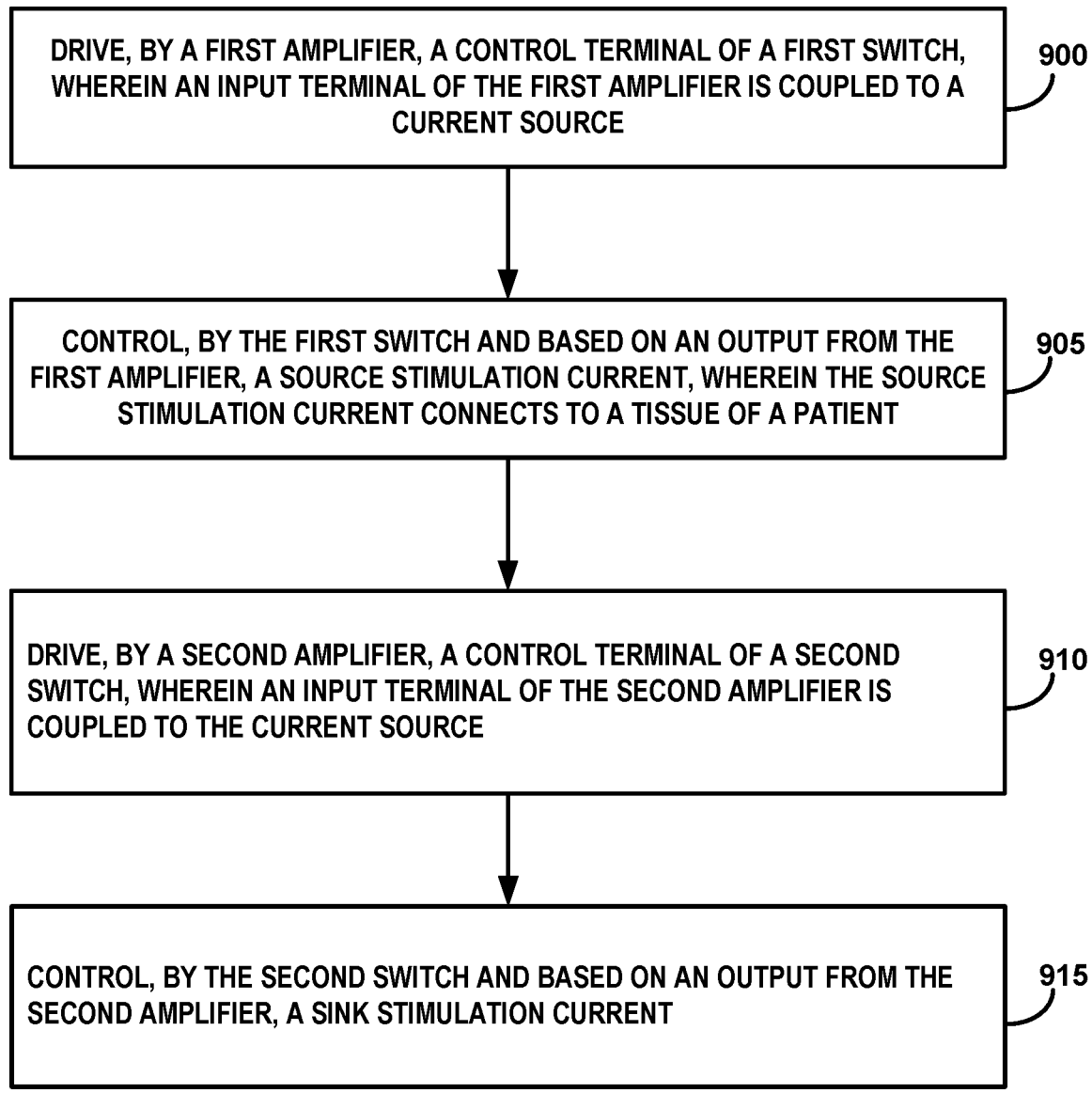
FIG. 9 is a flow chart illustrating an example operation of impedance measurement circuitry according to one or more techniques of this disclosure.

FIG. 9 is a flow diagram illustrating an example operation of an impedance measurement circuit, in accordance with one or more techniques of this disclosure. The blocks of FIG. 9 will be described in terms of FIGS. 2 and 3 unless otherwise noted.

As seen in the example of FIG. 9, amplifier 330 may drive a control terminal of switch P1 326 (900). The non-inverting input terminal of amplifier 330 is coupled to reference current 312, which is also coupled to the non-inverting input of amplifier 332. As described above in relation to FIGS. 3, 4 and 8 coupling the single reference current to the source stimulation circuit and the sink stimulation circuit may ensure the source current Istim_source 322 approximately equals Istim_sink 324.

Next, switch P1 326 may control source stimulation current Istim_source 322, based on the output from the amplifier 330. The source stimulation current may connect to tissue of a patient through switch matrix 320 (905).

Amplifier 332 may drive the control terminal of switch N1 328 to output Istim_sink 324 to an electrode in contact with the patient's tissue via switch matrix 320 (910). Switch N1 328, may control sink stimulation current, Istim_sink 324, based on the output from amplifier 332 (915). As described above, the magnitude of the sink stimulation current is approximately equal to a magnitude of the source stimulation current, and the source stimulation current and the sink stimulation current induce a voltage at the tissue of the patient. As described above in relation to FIGS. 6 and 7, the voltage at the star node may float with respect to the voltage of the stimulation current, and therefore the induced voltage measured by impedance measurement circuitry 120 may be less affected by the common mode capacitance on the star node.

The techniques described in this disclosure may be implemented, at least in part, in hardware, software, firmware or any combination thereof. For example, various aspects of the described techniques, such as processing circuitry 106 described above in relation to FIG. 2, may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer-readable media may include non-transitory computer-readable storage media and transient communication media. Computer readable storage media, which is tangible and non-transitory, may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media. It should be understood that the term "computer-readable storage media" refers to physical storage media, and not signals, carrier waves, or other transient media.

The techniques of this disclosure may also be described in the following examples.

Example 1: An impedance measurement device that comprises a source stimulation circuit that includes a first switch configured to control a source stimulation current; a first amplifier configured to drive a control terminal of the first switch; a sink stimulation circuit includes a second switch configured to control a sink stimulation current; a second amplifier configured to drive a control terminal of the second switch; a reference current coupled to the source stimulation circuit and the sink stimulation circuit, such that a magnitude of the source stimulation current approximately equals a magnitude of the sink stimulation current.

Example 2: The device of example 1, wherein: the source stimulation circuit receives power from a first power supply, the sink stimulation circuit receives power from a second power supply, and a voltage of the second power supply is level shifted such that, with respect to a ground reference voltage, the voltage of the second power supply is opposite in polarity to the first power supply and approximately equal to a voltage of the first power supply.

Example 3: The device of any of examples 1 and 2, wherein the first switch comprises a positive, metal oxide semiconductor field effect transistor (P-MOSFET), and the second switch comprises a negative MOSFET (N-MOSFET).

Example 4: The device of any combination of examples 1 through 3, wherein: an output terminal of the source stimulation circuit is configured to couple to tissue of a patient; an output terminal of the sink stimulation circuit is configured to couple to the tissue of the patient; the source stimulation current and the sink stimulation current are configured to induce a voltage at the tissue of the patient.

Example 5: The device of any combination of examples 1 through 4, wherein a non-inverting terminal of the first amplifier connects to a first terminal of the reference current; and wherein a non-inverting terminal of the second amplifier connects to a second terminal of the reference current.

Example 6: The device of any combination of examples 1 through 5, wherein the current source is a current mirror.

Example 7: The device of any combination of examples 1 through 6, further comprising a first monitoring circuit, configured to: determine whether a voltage at the control terminal of the first switch satisfies a threshold; in response to determining that the voltage at the control terminal satisfies the threshold, output an indication that the voltage satisfied the threshold.

Example 8: The device of any combination of examples 1 through 7, wherein the first monitor circuit comprises a comparator circuit.

Example 9: The device of any combination of examples 1 through 8, wherein to satisfy a threshold comprises the voltage at the control terminal of the first switch is less than the voltage threshold.

Example 10: The device of any combination of examples 1 through 9, wherein the threshold is a first threshold, the device further comprising a second monitoring circuit, configured to: determine whether a voltage at the control terminal of the second switch satisfies a second threshold; in response to determining that the voltage at the control terminal of the second switch satisfies the second threshold, output an indication that the voltage satisfied the second threshold.

Example 11: The device of any combination of examples 1 through 10, further comprising a warm-up circuit, wherein the warm-up circuit is configured to conduct a warm-up current a first time; wherein the first amplifier is configured to drive a control terminal of the first switch to output the source stimulation current at a second time, subsequent to the first time, and wherein the warm-up current is a predetermined portion of the source stimulation current.

Example 12: The device of any combination of examples 1 through 11, further comprising a disable circuit configured to disable the sink stimulation circuit.

Example 13: An implantable medical device comprising impedance measurement circuitry, wherein the impedance measurement circuitry comprises: a source stimulation circuit includes a first switch configured to control a source stimulation current; a first amplifier configured to drive a control terminal of the first switch; a sink stimulation circuit includes a second switch configured to control a sink stimulation current; a second amplifier configured to drive a control terminal of the second switch; a current source coupled to the source stimulation circuit and the sink stimulation circuit, such that a magnitude of the source stimulation current approximately equals a magnitude of the sink stimulation current.

Example 14: The implantable medical device of example 13, wherein the source stimulation circuit receives power from a first power supply, the sink stimulation circuit receives power from a second power supply, and a voltage of the second power supply is level shifted such that, with respect to a ground reference voltage, the voltage of the second power supply is opposite in polarity to the first power supply and approximately equal to a voltage of the first power supply.

Example 15: The implantable medical device of any of examples 13 and 14, wherein the first switch comprises a positive, metal oxide semiconductor field effect transistor (P-MOSFET), and the second switch comprises a negative MOSFET (N-MOSFET).

Example 16: The implantable medical device of any combination of examples 13 through 15, wherein: an output terminal of the source stimulation circuit is configured to couple to tissue of a patient; an output terminal of the sink stimulation circuit is configured to couple to the tissue of the patient; the source stimulation current and the sink stimulation current are configured to induce a voltage at the tissue of the patient.

Example 17: The implantable medical device of any combination of examples 13 through 16, further comprising sensing circuitry configured to: measure the voltage induced at the tissue of the patient; and calculate a lead impedance based on: the magnitude of the source stimulation current; the magnitude of the sink stimulation current; and the measured voltage induced at the tissue of the patient.

Example 18: The implantable medical device of any combination of examples 13 through 17, further comprising switching circuitry configured to: output the source stimulation current to a first electrode of a plurality of electrodes; output the sink stimulation current to a second electrode of the plurality of electrodes; measure the induced voltage between a third electrode and a fourth electrode of the plurality of electrodes.

Example 19: The implantable medical device of any combination of examples 13 through 18, wherein the first electrode is the same electrode as the third electrode and the second electrode is the same electrode as the fourth electrode.

Example 20: The implantable medical device of any combination of examples 13 through 19, wherein a non-inverting terminal of the first amplifier connects to a first terminal of the reference current; and wherein a non-inverting terminal of the second amplifier connects to a second terminal of the reference current.

Example 21: The implantable medical device of any combination of examples 13 through 20, the impedance measurement circuitry further comprising a first monitoring circuit, configured to: determine whether a voltage at the control terminal of the first switch satisfies a threshold; in response to determining that the voltage at the control terminal satisfies the threshold, output an indication that the voltage satisfied the threshold.

Example 22: The implantable medical device of any combination of examples 13 through 21, the impedance measurement circuitry further comprising a warm-up circuit, wherein the warm-up circuit is configured to conduct a warm-up current at a first time; wherein the first amplifier is configured to drive a control terminal of the first switch to output the source stimulation current at a second time, subsequent to the first time, and wherein the warm-up current is a predetermined fraction of the source stimulation current.

Example 23: A method includes driving, by a first amplifier, a control terminal of a first switch, wherein an input terminal of the first amplifier is coupled to a reference current; controlling, by the first switch and based on an output from the first amplifier, a source stimulation current, wherein the source stimulation current connects to a tissue of a patient; driving, by a second amplifier, a control terminal of a second switch, wherein an input terminal of the second amplifier is coupled to the reference current; controlling, by the second switch and based on an output from the second amplifier, a sink stimulation current, wherein: the sink stimulation current connects to the tissue of the patient, a magnitude of the sink stimulation current is approximately equal to a magnitude of the source stimulation current, the source stimulation current and the sink stimulation current induce a voltage at the tissue of the patient.

Various examples of the disclosure have been described. These and other examples are within the scope of the following claims.

What is claimed is:

1. An impedance measurement device, the device comprising:
   a source stimulation circuit comprising:
   a first switch configured to control a source stimulation current; and a first amplifier configured to drive a control terminal of the first switch;
a sink stimulation circuit comprising:
a second switch configured to control a sink stimulation current; and
a second amplifier configured to drive a control terminal of the second switch; and
a reference current coupled to both the first amplifier of the source stimulation circuit and the second amplifier of the sink stimulation circuit, such that a magnitude of the source stimulation current approximately equals a magnitude of the sink stimulation current.

2. The device of claim 1, wherein:
the source stimulation circuit receives power from a first power supply,
the sink stimulation circuit receives power from a second power supply, and
a voltage of the second power supply is level shifted such that, with respect to a ground reference voltage, the voltage of the second power supply is opposite in polarity to the first power supply and approximately equal to a voltage of the first power supply.

3. The device of claim 1, wherein the first switch comprises a positive, metal oxide semiconductor field effect transistor (P-MOSFET), and the second switch comprises a negative MOSFET (N-MOSFET).

4. The device of claim 1, wherein:
an output terminal of the source stimulation circuit is configured to couple to tissue of a patient;
an output terminal of the sink stimulation circuit is configured to couple to the tissue of the patient; and
the source stimulation current and the sink stimulation current are configured to induce a voltage at the tissue of the patient.

5. The device of claim 1,
wherein a non-inverting terminal of the first amplifier connects to a first terminal of the reference current; and
wherein a non-inverting terminal of the second amplifier connects to a second terminal of the reference current.

6. The device of claim 5, wherein the reference current is implemented as a current mirror.

7. The device of claim 1, further comprising a first monitoring circuit, configured to:
determine whether a voltage at the control terminal of the first switch satisfies a threshold; and
in response to determining that the voltage at the control terminal satisfies the threshold, output an indication that the voltage satisfied the threshold.

8. The device of claim 7, wherein the first monitor circuit comprises a comparator circuit.

9. The device of claim 7, wherein to satisfy a threshold comprises the voltage at the control terminal of the first switch exceeds the threshold.

10. The device of claim 7, wherein the threshold is a first threshold, the device further comprising a second monitoring circuit, configured to:
determine whether a voltage at the control terminal of the second switch satisfies a second threshold; and
in response to determining that the voltage at the control terminal of the second switch satisfies the second threshold, output an indication that the voltage satisfied the second threshold.

11. The device of claim 1, further comprising a disable circuit configured to disable the sink stimulation circuit.

12. An implantable medical device comprising impedance measurement circuitry, wherein the impedance measurement circuitry comprises:
a source stimulation circuit comprising:
a first switch configured to control a source stimulation current; and
a first amplifier configured to drive a control terminal of the first switch;
a sink stimulation circuit comprising:
a second switch configured to control a sink stimulation current; and
a second amplifier configured to drive a control terminal of the second switch; and
a reference current coupled to both the first amplifier of the source stimulation circuit and the second amplifier of the sink stimulation circuit, such that a magnitude of the source stimulation current approximately equals a magnitude of the sink stimulation current.

13. The implantable medical device of claim 12,
wherein the source stimulation circuit receives power from a first power supply,
the sink stimulation circuit receives power from a second power supply, and
a voltage of the second power supply is level shifted such that, with respect to a ground reference voltage, the voltage of the second power supply is opposite in polarity to the first power supply and approximately equal to a voltage of the first power supply.

14. The implantable medical device of claim 12, wherein the first switch comprises a positive, metal oxide semiconductor field effect transistor (P-MOSFET), and the second switch comprises a negative MOSFET (N-MOSFET).

15. The implantable medical device of claim 12, wherein:
an output terminal of the source stimulation circuit is configured to couple to tissue of a patient;
an output terminal of the sink stimulation circuit is configured to couple to the tissue of the patient; and
the source stimulation current and the sink stimulation current are configured to induce a voltage at the tissue of the patient.

16. The implantable medical device of claim 12, further comprising sensing circuitry configured to:
measure the voltage induced at the tissue of the patient; and
calculate a lead impedance based on:
the magnitude of the source stimulation current;
the magnitude of the sink stimulation current; and
the measured voltage induced at a tissue of the patient.

17. The implantable medical device of claim 16, further comprising switching circuitry configured to:
output the source stimulation current to a first electrode of a plurality of electrodes;
output the sink stimulation current to a second electrode of the plurality of electrodes; and
measure the induced voltage between a third electrode and a fourth electrode of the plurality of electrodes.

18. The implantable medical device of claim 17, wherein the first electrode is the same electrode as the third electrode and the second electrode is the same electrode as the fourth electrode.

19. The implantable medical device of claim 12, wherein, the implantable medical device is configured to automatically change from a first electrode vector to a second electrode vector based on the measured voltage.

20. The implantable medical device of claim 12,
wherein a non-inverting terminal of the first amplifier connects to a first terminal of the reference current; and
wherein a non-inverting terminal of the second amplifier connects to a second terminal of the reference current.

21. The implantable medical device of claim 12, the impedance measurement circuitry further comprising a first monitoring circuit, configured to:
- determine whether a voltage at the control terminal of the first switch satisfies a threshold; and
- in response to determining that the voltage at the control terminal satisfies the threshold, output an indication that the voltage satisfied the threshold.

22. The implantable medical device of claim 21, wherein the impedance measurement circuitry is configured to determine, in a single impedance measurement and based on whether the voltage at the control terminal of the first switch satisfied the threshold, which electrode of a plurality of electrodes is connected to an intact pathway.

23. The implantable medical device of claim 21, wherein, in response to the indication that the voltage satisfied the threshold, the implantable medical device is configured to output an alert to a user of the of the implantable medical device.

24. A method comprising:
- driving, by a first amplifier, a control terminal of a first switch, wherein an input terminal of the first amplifier is coupled to a reference current;
- controlling, by the first switch and based on an output from the first amplifier, a source stimulation current, wherein the source stimulation current connects to a tissue of a patient;
- driving, by a second amplifier, a control terminal of a second switch, wherein an input terminal of the second amplifier is coupled to the reference current; and
- controlling, by the second switch and based on an output from the second amplifier, a sink stimulation current, wherein:
  - the sink stimulation current connects to the tissue of the patient,
  - a magnitude of the sink stimulation current is approximately equal to a magnitude of the source stimulation current, and
  - the source stimulation current and the sink stimulation current induce a voltage at the tissue of the patient.

25. An implantable medical device comprising impedance measurement circuitry, wherein the impedance measurement circuitry comprises:
- a source stimulation circuit comprising:
  - a first switch configured to control a source stimulation current; and
  - a first amplifier configured to drive a control terminal of the first switch;
- a sink stimulation circuit comprising:
  - a second switch configured to control a sink stimulation current; and
  - a second amplifier configured to drive a control terminal of the second switch;
- a reference current coupled to both the first amplifier of the source stimulation circuit and the second amplifier of the sink stimulation circuit, such that a magnitude of the source stimulation current approximately equals a magnitude of the sink stimulation current; and
- sensing circuitry configured to:
  - measure the voltage induced at the tissue of the patient; and
  - calculate a lead impedance based on:
    - the magnitude of the source stimulation current;
    - the magnitude of the sink stimulation current; and
    - the measured voltage induced at a tissue of the patient.

* * * * *